US009430933B2

(12) United States Patent
Fadell et al.

(10) Patent No.: US 9,430,933 B2
(45) Date of Patent: Aug. 30, 2016

(54) VISUAL AND AUDITORY USER NOTIFICATION METHODS FOR SMART-HOME HAZARD DETECTOR

(71) Applicant: Google Inc., Mountain View, CA (US)

(72) Inventors: Anthony Michael Fadell, Portola Valley, CA (US); Matthew Lee Rogers, Los Gatos, CA (US); David Sloo, Menlo Park, CA (US); Maxime Veron, San Jose, CA (US); Sophie Le Guen, Burlingame, CA (US); Nick Webb, Menlo Park, CA (US)

(73) Assignee: Google Inc., Mountain View, CA (US)

( * ) Notice: Subject to any disclaimer, the term of this patent is extended or adjusted under 35 U.S.C. 154(b) by 19 days.

(21) Appl. No.: 14/508,409

(22) Filed: Oct. 7, 2014

(65) Prior Publication Data

US 2015/0097681 A1    Apr. 9, 2015

Related U.S. Application Data

(60) Provisional application No. 61/887,963, filed on Oct. 7, 2013, provisional application No. 61/887,969, filed on Oct. 7, 2013.

(51) Int. Cl.
*G08B 17/10*    (2006.01)
*G08B 25/00*    (2006.01)
(Continued)

(52) U.S. Cl.
CPC ......... *G08B 25/008* (2013.01); *F24F 11/0009* (2013.01); *G01N 27/02* (2013.01); *G01N 27/121* (2013.01); *G01N 33/004* (2013.01); *G01N 33/0031* (2013.01); *G08B 3/10* (2013.01);
(Continued)

(58) Field of Classification Search
CPC ... G08B 29/02; F24F 11/0009; G01N 27/02; G01N 27/121; G01N 33/0031
USPC .......................................................... 340/628
See application file for complete search history.

(56) References Cited

U.S. PATENT DOCUMENTS 5,461,365 A    10/1995 Schlager et al.
8,375,118 B2 *  2/2013 Hao ................... G05B 15/02
                                                    709/223
(Continued)

OTHER PUBLICATIONS

International Search Report and Written Opinion mailed Jan. 9, 2015 for PCT/US2014/059482 filed on Oct. 7, 2014, 20 pages.
(Continued)

*Primary Examiner* — Eric M Blount
(74) *Attorney, Agent, or Firm* — Kilpatrick Townsend & Stockton LLP

(57) ABSTRACT

Hazard detector for providing a pre-alarm of a developing hazardous condition includes a detection module that detects a hazard level of smoke or carbon monoxide, a storage module that stores a pre-alarm threshold and an emergency threshold, a light source that generates light in a first color, a second color, and a third color, a speaker that generates an audible sound, a horn that generates an audible alarm that a higher volume than the speaker, and a processing module. The processing module receives the detected hazard level and compares it with the pre-alarm threshold and the emergency threshold. The processing module determines that the hazard level is greater than the pre-alarm threshold and less than the emergency threshold and generates an audible pre-alarm speech via the speaker that warns of the developing hazardous condition. The processing module also activates the light source in the second color.

19 Claims, 20 Drawing Sheets

(51) Int. Cl.

| | |
|---|---|
| *G08B 21/18* | (2006.01) |
| *G01N 27/02* | (2006.01) |
| *G01N 27/12* | (2006.01) |
| *G01N 33/00* | (2006.01) |
| *G08B 17/117* | (2006.01) |
| *G08B 29/18* | (2006.01) |
| *G08B 5/36* | (2006.01) |
| *G08B 3/10* | (2006.01) |
| *G08B 21/14* | (2006.01) |
| *H04L 12/28* | (2006.01) |
| *G08B 5/22* | (2006.01) |
| *G08B 21/12* | (2006.01) |
| *F24F 11/00* | (2006.01) |
| *G08B 25/01* | (2006.01) |
| *G08B 29/02* | (2006.01) |
| *G08B 29/04* | (2006.01) |
| *G08B 25/08* | (2006.01) |

(52) U.S. Cl.
CPC . *G08B5/22* (2013.01); *G08B 5/36* (2013.01); *G08B 17/10* (2013.01); *G08B 17/117* (2013.01); *G08B 21/12* (2013.01); *G08B 21/14* (2013.01); *G08B 21/18* (2013.01); *G08B 21/182* (2013.01); *G08B 25/012* (2013.01); *G08B 29/02* (2013.01); *G08B 29/04* (2013.01); *G08B 29/185* (2013.01); *H04L 12/2803* (2013.01); *H04L 12/2818* (2013.01); *G08B 25/08* (2013.01)

(56) References Cited

U.S. PATENT DOCUMENTS

| | | | |
|---|---|---|---|
| 8,442,693 B2 | 5/2013 | Mirza et al. | |
| 8,539,567 B1 | 9/2013 | Logue et al. | |
| 9,049,567 B2 * | 6/2015 | Le Guen | G08B 25/10 |
| 2003/0234725 A1 | 12/2003 | Lemelson et al. | |
| 2004/0135683 A1 | 7/2004 | Sakai | |
| 2005/0253709 A1 | 11/2005 | Baker | |
| 2007/0045433 A1 | 3/2007 | Chapman et al. | |
| 2007/0084941 A1 | 4/2007 | de Pauw et al. | |
| 2008/0015740 A1 * | 1/2008 | Osann | G05B 15/02 |
| | | | 700/276 |
| 2008/0266064 A1 | 10/2008 | Curran et al. | |
| 2009/0051552 A1 | 2/2009 | Chabanis et al. | |
| 2009/0077623 A1 | 3/2009 | Baum et al. | |
| 2010/0070089 A1 | 3/2010 | Harrod et al. | |
| 2013/0154823 A1 | 6/2013 | Ostrer et al. | |
| 2013/0241697 A1 * | 9/2013 | Baumert | H04W 4/001 |
| | | | 340/8.1 |
| 2014/0266669 A1 | 9/2014 | Fadell et al. | |

OTHER PUBLICATIONS

International Search Report and Written Opinion mailed Jan. 12, 2015 for PCT/US2014/059498 filed on Oct. 7, 2014, 14 pages.

* cited by examiner

| Light State | Definition |
|---|---|
| 1401 (blue) | A blue glow is emitted when awake and ready to be configured.<br><br>Before and after a manual test, a blue glow is emitted. |
| 1402 (green) | A green pulse is emitted during and after setup to confirm communication with the Internet and to signal that setup is complete.<br><br>A green pulse is emitted at night when the lights are turned off to signal that the batteries and sensors are functioning properly. |
| 1403 (white) | White light is emitted when a path-light feature is triggered, such as based on a detected ambient brightness level below a threshold and user motion being detected. |

FIG. 14

| Light State | Definition |
|---|---|
| 1404 (yellow) | A low level of smoke or carbon monoxide (CO) has been detected. A "heads-up" (pre-alert) message may be output that indicates the type of danger and the location.<br><br>If a heads-up (pre-alert) message is silenced due to a button press or wave, a yellow glow is output. The device continues to monitor for hazards.<br><br>If a low battery level is detected or a sensor is having a problem or is expired, a pulsed yellow light will be output when the ambient brightness level drops below a threshold level.<br><br>If a manual test is failed, a yellow glow is emitted along with an indication of the problem. |
| 1405 (red) | A dangerous level of smoke or carbon monoxide has been detected. A loud alarm and voice is output identifying the location and type of problem. The alarm sound and the voice message may be interleaved such that the two outputs alternate being output.<br><br>If the device is silenced by a gesture or button press, the device will remain quiet while outputting a red glow. The structure will continue to be monitored for hazards. |
| 1406 (green) | A small, separate light may be illuminated when power is being received from a structure's wired electrical system (e.g., 140 V AC). |

FIG. 15

| Light State | Audio Output | Definition |
|---|---|---|
| 1407 — Blue pulses | "Hi from [device]" | The device is ready to be set up. |
| 1408 — Blue pulses | "Press to Test" | Pulses to indicate sensors will be tested, battery will be tested, network connection will be tested, and wireless communication with other wireless devices (e.g., smart hazard detectors) will be tested. |
| 1409 — Yellow Pulses | Ding/Bell sound interleaved with "Heads-up. There's smoke in the [room name]. The alarm may sound." | Smoke levels are rising. |

FIG. 16

| Light State | Audio Output | Definition |
|---|---|---|
| 1416 → Green pulses | "Carbon Monoxide is clearing in the [room name]." | Conditions are returning to normal. |
| 1417 → Yellow pulses | A single chirp sounds every 30 seconds.<br>"The battery is very low in the [room name]. Replace the battery soon." | The batteries are depleted and must be replaced. |
| 1418 → Yellow pulses | "The sensors have failed in the [room name]. Replace the device now." | There is a problem with one or more sensors. |

FIG. 19

| Light State | Audio Output | Definition |
|---|---|---|
| 1419 — Yellow pulses | "The battery is low in [room name]. Replace the battery soon." | The batteries are low and should be replaced soon. |
| 1420 — Yellow pulses | Two chirps may sound every minute. "The device has expired. Replace it now." | The device has reached the end of its life. |
| 1421 — Yellow pulses | "Disconnected from the Internet" | The device is no longer connected to the Internet. |

FIG. 20

| Type of Alarm | Can be silenced | Cannot be silenced |
|---|---|---|
| Heads-up (pre-alert) for smoke or carbon monoxide | By waving (wave-to-hush gesture) or pressing a button on the device | By regulation (law), a heads-up is permitted to be silenced from the device that triggered the alarm. An alert as to which room is given. |
| Smoke emergency (alert) alarms | By waving (a wave-to-hush gesture) or pressing a button on the device | Dense or dangerous smoke levels will override the alarm being silenced. A continuous alarm will sound. |
| Carbon monoxide emergency (alert) alarms | Can be silenced by waving (wave-to-hush gesture) or pressing a button on the device. If dangerous levels of CO are reached with a predefined period of time (e.g., 6 minutes), the alarm will sound again. | |

FIG. 21

VISUAL AND AUDITORY USER NOTIFICATION METHODS FOR SMART-HOME HAZARD DETECTOR

CROSS-REFERENCES TO RELATED APPLICATIONS

This application claims the benefit of U.S. Provisional Patent Application No. 61/887,963, filed Oct. 7, 2013, entitled "HAZARD DETECTION IN A SMART-SENSORED HOME," and U.S. Provisional Patent Application No. 61/887,969, filed Oct. 7, 2013, entitled "USER-FRIENDLY DETECTION UNIT," the entire disclosures of which are hereby incorporated by reference for all purposes.

BACKGROUND

1. The Field of the Invention

The present invention generally relates to hazard detection. More specifically, the present invention relates to hazard detection units that provide pre-alarms for developing hazardous conditions.

2. The Relevant Technology

Hazard detectors use a variety of sensors to detect substances in the air that are harmful or indicate the development of a hazardous situation. For example, carbon monoxide (CO) and radon gas are substances that can be harmful to humans and animals if exposed to high amounts. However, these substances are difficult to detect with the human senses because they are colorless, odorless, and tasteless. A hazard detector can detect the presence of these substances and prevent the harmful effects of exposure by alarming a user. In other instances, a substance such as smoke, while not necessarily harmful in and of itself, can indicate the development of a hazardous situation, such as fire.

Hazard detectors are certified under standards defined by a governing body, such as the Occupational Safety and Health Administration (OSHA), or companies that perform safety testing, such as Underwriters Laboratories (UL). For example, UL defines thresholds for when smoke detectors and CO detectors should sound an alarm. UL also defines the characteristics of the alarm, such as the volume, pitch, and pattern of the sound.

BRIEF SUMMARY

In one embodiment, a hazard detector for providing a pre-alarm of a developing hazardous condition is presented. The hazard detector includes a detection module, a storage module, a light source, a speaker, a horn, and a processing module. The processing module is coupled to the detection module, the storage module, the light source, the speaker, and the horn. The detection module is configured to detect a hazard level that indicates an amount of smoke or carbon monoxide (CO) present at the hazard detector. The storage module is configured to store a pre-alarm threshold and an emergency threshold. The pre-alarm threshold is less than the emergency threshold. The light source is configured to generate light in a first color, a second color, and a third color. The second color is between the first color and the third color on the color spectrum. The speaker is configured to generate an audible sound and the horn is configured to generate an audible alarm at a higher volume than the speaker.

The processing module is configured to receive the detected hazard level from the detection module. The processing module compares the detected hazard level with the pre-alarm threshold and the emergency threshold and determines that the detected hazard level is greater than the pre-alarm threshold and less than the emergency threshold. An audible pre-alarm speech is generated via the speaker in response to determining that the detected hazard level is greater than the pre-alarm threshold and less than the emergency threshold. The audible pre-alarm speech includes content that warns of the developing hazardous condition. The processing module further activates the light source in the second color in response to determining that the detected hazard level is greater than the pre-alarm threshold and less than the emergency threshold.

In another embodiment, a method is presented for providing a pre-alarm of a developing hazardous condition. The method includes detecting a first hazard level that indicates an amount of smoke or CO present at a hazard detector. The first hazard level is compared with an emergency threshold and it is determined that the first hazard level is greater than the emergency threshold. A horn that generates an audible alarm is activated in response to determining that the first hazard level is greater than the emergency threshold. Further, a first light source that generates a red colored light is activated in response to determining that the first hazard level is greater than the emergency threshold.

A second hazard level is detected and is compared with the emergency threshold. It is determined that the second hazard level is less than the emergency threshold. The second hazard level is compared with a pre-alarm threshold that is less than the emergency threshold and it is determined that the second hazard level is greater than the pre-alarm threshold. A second light source that generates a yellow colored light is activated in response to determining that the second hazard level is greater than the pre-alarm threshold and less than the emergency threshold. Further, a speaker that generates an audible pre-alarm speech at a lower volume than the horn is activated in response to determining that the second hazard level is greater than the pre-alarm threshold and less than the emergency threshold. The audible pre-alarm speech includes content that warns of the developing hazardous condition.

In a further embodiment, a non-transitory computer-readable medium is presented. The computer-readable medium has instructions stored therein, which when executed cause a computer to perform a set of operations. The set of operations include detecting a hazard level that indicates an amount of smoke or CO present at a hazard detector. The hazard level is compared with an emergency threshold and it is determined that the hazard level is less than the emergency threshold. The set of operations further include comparing the hazard level with a pre-alarm threshold that is less than the emergency threshold and determining that the hazard level is greater than the pre-alarm threshold. A light source that generates light in a first color, a second color, and a third color is activated in response to determining that the hazard level is greater than the pre-alarm threshold and less than the emergency threshold. The light source is activated in the second color which is between the first color and the third color on the color spectrum. A speaker that generates an audible pre-alarm speech is also activated in response to determining that the hazard level is greater than the pre-alarm threshold and less than the emergency threshold. The audible pre-alarm speech includes content that warns of a developing hazardous condition.

In one embodiment, a hazard detector for providing a pre-alarm of a developing hazardous condition is presented. The hazard detector includes means for detecting a hazard level that indicates an amount of smoke or CO present at a hazard detector. The hazard detector further includes means for comparing the hazard level with an emergency threshold, means for determining that the hazard level is less than the emergency threshold, means for comparing the hazard level with a pre-alarm threshold that is less than the emergency threshold, and means for determining that the hazard level is greater than the pre-alarm threshold. The hazard detector also includes means for generating light in a first color, a second color, and a third color in response to determining that the hazard level is greater than the pre-alarm threshold and less than the emergency threshold. The second color is between the first color and the third color on the color spectrum. The hazard detector further includes means for generating an audible pre-alarm speech in response to determining that the hazard level is greater than the pre-alarm threshold and less than the emergency threshold. The audible pre-alarm speech includes content that warns of a developing hazardous condition.

BRIEF DESCRIPTION OF THE DRAWINGS

A further understanding of the nature and advantages of various embodiments may be realized by reference to the following figures. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

FIGS. 14-20 represent various illumination states and audio messages that may be output by a hazard detector.

FIG. 21 illustrates a chart indicative of various situations in which pre-alert messages and sounds may be silenced and situations in which messages and sounds cannot be silenced.

DETAILED DESCRIPTION OF THE INVENTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

Conventional hazard detectors operate solely based on thresholds set by the standards of governing bodies and safety testing companies. The thresholds define a level or amount for each hazardous substance at which an alarm should be sounded. These conventional hazard detectors are limited and simplistic in operation. For example, their mode of operation is binary, either sound the alarm or do not sound the alarm, and the decision of whether to sound the alarm is based on readings from only one type of sensor. Several disadvantages are associated with these simple and conventional hazard detectors. For example, users are often subjected to false alarms caused by conditions that are not actually hazardous. Alternatively, conventional hazard detectors sometimes fail to sound the alarm for truly hazardous conditions that warrant genuine concern because the standardized thresholds for triggering the alarm have not been met.

The embodiments of the invention described herein below overcome the disadvantages of the prior art by providing a hazard detector that gives a pre-alarm ("Heads Up" notification) of a developing hazardous condition. The embodiments include a hazard detector that compares a detected hazard level with a pre-alarm threshold and an emergency threshold. In one embodiment, the emergency threshold corresponds to a threshold defined by a standard and the pre-alarm threshold is less than the emergency threshold. If it is determined that the detected hazard level is greater than the pre-alarm threshold and less than the emergency threshold, a speaker is activated to generate a pre-alarm speech at a lower volume than the alarm. A light source is also activated in a less concerning color than the color of the light that is activated for alarms.

Figure 1:
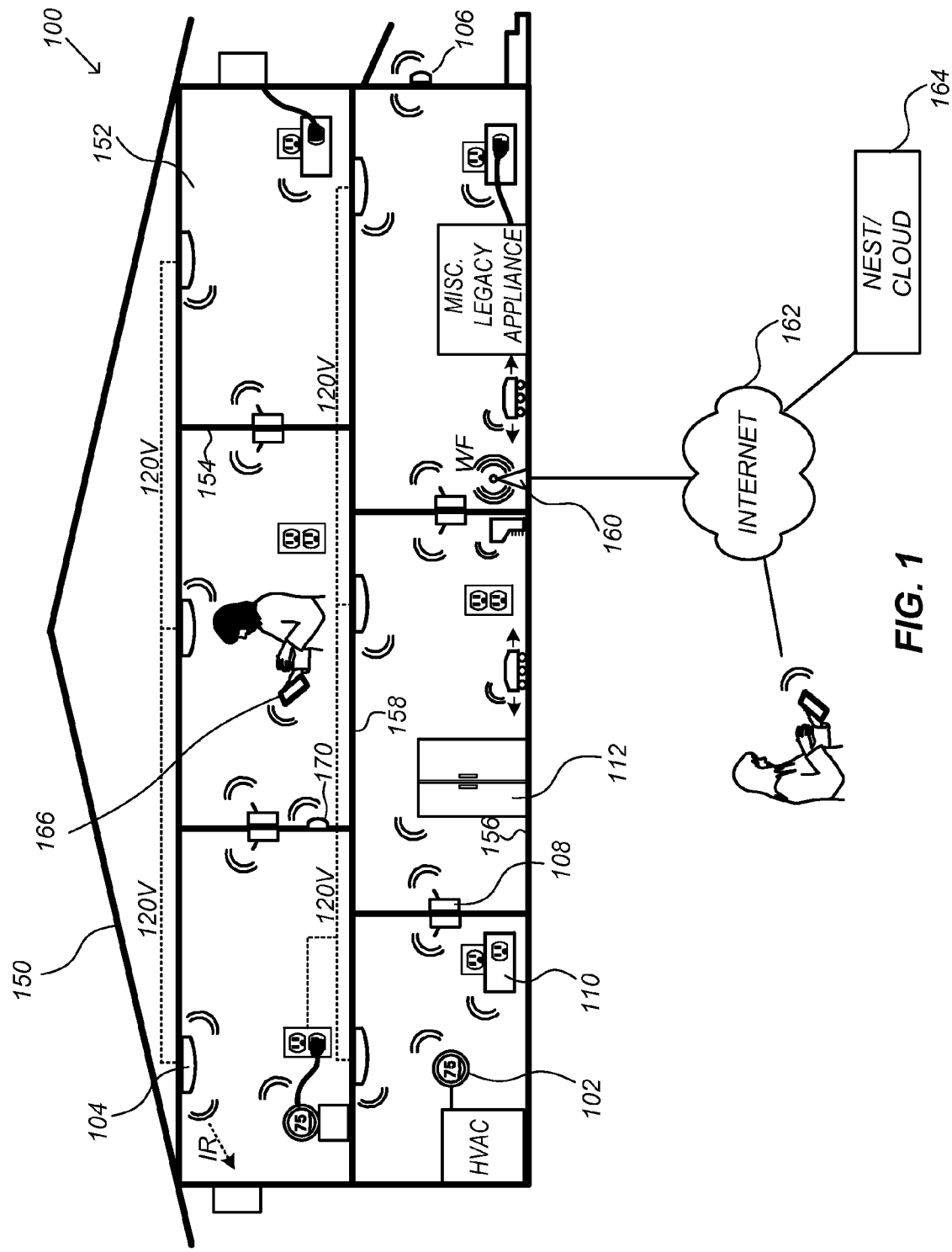
FIG. 1 is an example of a smart-home environment within which one embodiment of a system for providing a pre-alarm of a developing hazardous condition can be implemented.

FIG. 1 is an example of a smart-home environment 100 within which one embodiment of a system for providing a pre-alarm of a developing hazardous condition can be implemented. The depicted smart-home environment 100 includes an enclosure 150, which can be, e.g., a house, office building, hotel, retail store, garage, or mobile home. The system can also be implemented in a smart-home environment 100 that does not include an entire enclosure 150, such as an apartment, condominium, or office space.

The depicted enclosure 150 includes a plurality of rooms 152, separated at least partly from each other via walls 154. The walls 154 can include interior walls or exterior walls. Each room can further include a floor 156 and a ceiling 158. Devices can be mounted on, integrated with and/or supported by a wall 154, floor 156 or ceiling 158. Further, the smart home environment can include devices outside of the actual enclosure 150, such as a pool heater or irrigation system.

The smart-home environment 100 includes a plurality of intelligent, multi-sensing, network-connected devices (hereinafter referred to as "the smart devices") that can integrate seamlessly with each other and with a computer server system 164, such as a cloud-computing system. The smart devices can include smart thermostats 102, smart hazard detectors 104, smart entryway devices 106 (e.g., doorbells or intercoms), smart wall switches 108, smart wall plug interfaces 110, and smart appliances 112, such as refrigerators, stoves and/or ovens, televisions, washers, dryers, lights, stereos, intercom systems, garage-door openers, floor fans, ceiling fans, wall air conditioners, pool heaters, irrigation systems, security systems, and so forth.

Any of the smart devices in the smart-home environment can include any number of sensors. For example, smart appliances 112 can include sensors that detect when they are being used. Additionally, a motion or occupancy sensor, such as an ultrasonic, passive infrared (PIR), or optical sensor, can be included in any of the smart devices to detect user activity and movement. Some smart devices will also have sensors specific to the device. For example, a smart light can include an ambient light sensor, such as a photoresistor or a single-pixel sensor that measures light in the room. Smart hazard detectors 104 can include smoke/fire/heat sensors, carbon monoxide/dioxide sensors, radon gas detectors, ambient light sensors, temperature sensors, humidity sensors, and the like. Any smart device can also include a processor for processing data from the sensors or other devices.

Each smart device is also equipped with communications ports or transceivers for communicating data with other smart devices. In one embodiment, the devices establish a mesh network for communication between devices. In another embodiment, the devices can connect, via a router or gateway 160, to a private network or the internet 162, including any computer server system 164 and computing device that is connected to the same network. Data can be transferred via any wireless (e.g., Wi-Fi, ZigBee, 6LoWPAN, etc.) or wired (CAT6 Ethernet, HomePlug, etc.) protocols.

By virtue of network connectivity, one or more of the smart devices can further allow a user to interact with the device even if the user is not proximate to the device. For example, a user can communicate with a device using a computer (e.g., a desktop computer) or mobile device (e.g., a smartphone, laptop computer, or tablet) 166. A webpage or native mobile app can be configured to receive input from the user and control the device based on the input. The webpage or mobile app can also present information about the device's operation to the user. For example, the user can view the status of a smart hazard detector or a history of notifications generated by the smart hazard detector. The user can be in the enclosure during this remote communication or outside the enclosure.

Figure 2:
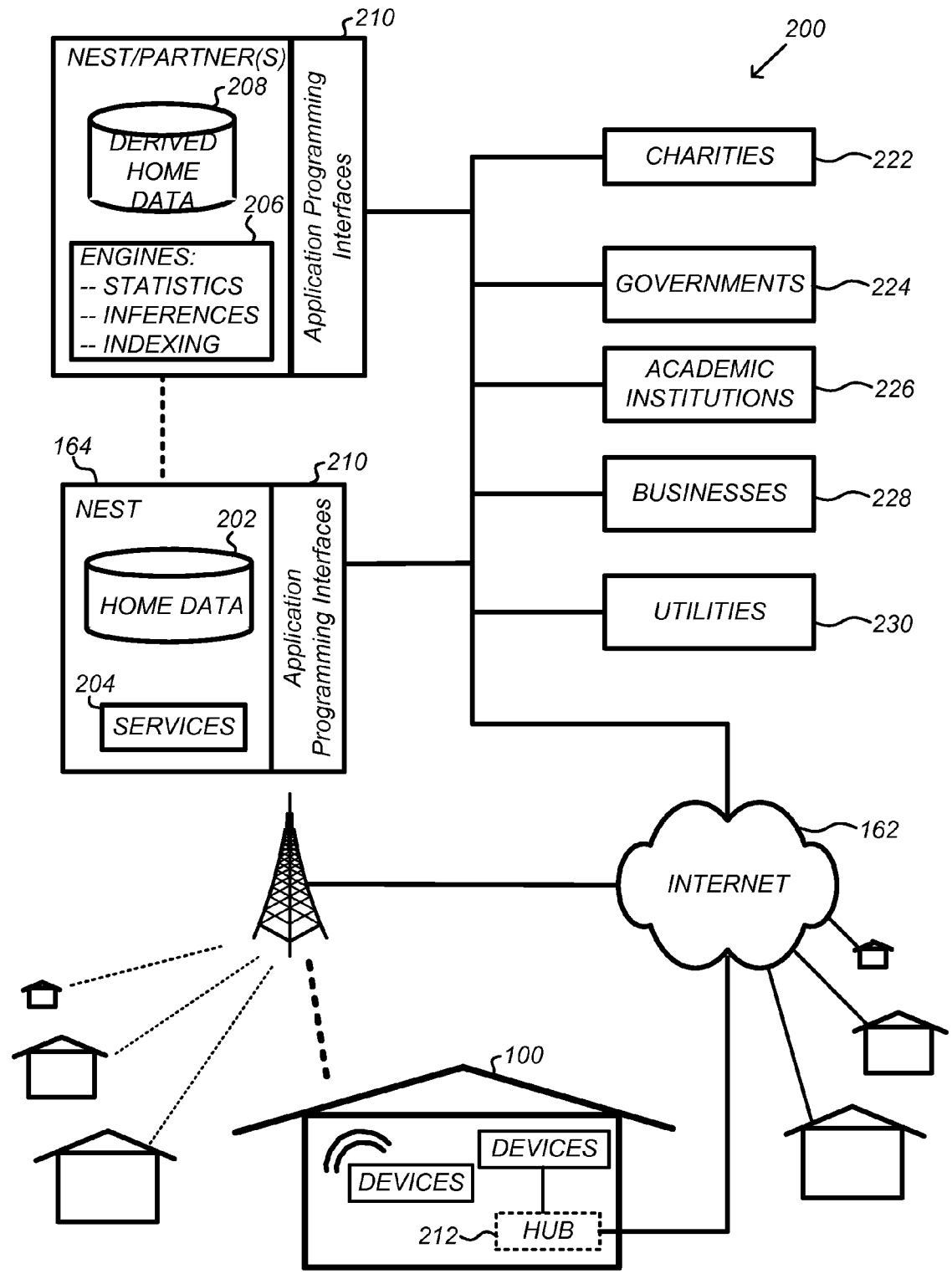
FIG. 2 is a network-level view of one embodiment of a system for providing a pre-alarm of a developing hazardous condition.

FIG. 2 is a network-level view of one embodiment of a system 200 for providing a pre-alarm of a developing hazardous condition. System 200 includes computer server system 164. Smart devices can communicate with the computer server system 164 via a private network or the internet 162. Smart devices can transmit home data 202, including user data and user activity data, to computer server system 164 for processing or storage. More specifically, home data 202 can include power consumption data, occupancy data, HVAC settings and usage data, carbon monoxide levels data, smoke levels data, volatile organic compounds levels data, sleeping schedule data, cooking schedule data, inside and outside temperature humidity data, television viewership data, inside and outside noise level data, etc.

The computer server system 164 can further provide one or more services 204. The services 204 can include customized hazard notifications, software updates, customer support, sensor data collection/logging, remote access, remote or distributed control, or use suggestions (e.g., based on collected home data 202 to improve performance, reduce utility cost, etc.). To facilitate these services, users can register the smart devices in their home or enclosure with the computer server system 164. Computer server system 164 can associate the smart devices with an account during the registration process. The account can be user specific or specific to a home or enclosure that includes multiple users, and a unique identification of each smart device can be stored in the account. In one embodiment, the user's mobile device or other computing device can also be associated with the account during registration. In another embodiment, one or more username and password is associated with the account during registration. The user can then use the username and password to log in on the mobile or computing device, and computer server system 164 can use the account to authorize the user's mobile or computing device for the services 204. Any identifying information can be used to log in and authorize users and their computing devices. For example, the mobile or computing device can include a fingerprint scanner, and the user logs in using their fingerprint. Data associated with the services 204, such as account data, can be stored at the computer server system 164.

System 200 includes a processing engine 206, which can be concentrated at a single server or distributed among several different computing entities without limitation. A single server can also include multiple engines for performing different processing tasks. The processing engine 206 can receive data from smart devices, index and store the data, or process the data to generate customized notifications or statistics. The processed data can be stored as derived home data 208. Results of the processing can be transmitted back to the device that provided the home data, to other devices, to a server providing a webpage to a user of the device, or to other non-device entities. For example, hazard events generated by smart hazard detectors can be received and processed by the processing engine 206 before being transmitted to a user device via the Internet 162. In this manner, the processing engine 206 can be configured and programmed to derive a variety of useful information from the home data 202.

In some embodiments, to encourage innovation and research and to increase products and services available to users, system 200 provides application programming interfaces (APIs) 210 to third parties, such as charities 222, governmental entities 224 (e.g., emergency response units such as a fire department or police department, the Food and Drug Administration, or the Environmental Protection Agency), academic institutions 226 (e.g., university researchers), businesses 228 (e.g., security or fire monitoring service providers, social network providers, device warranty or equipment service providers, or providers of targeted advertisements based on home data), utility companies 230, and other third parties. The APIs 210 permit third-party systems to communicate with the computer server system 164, providing access to the services 204, the processing engine 206, the home data 202, and the derived home data 208. This allows third-party applications to submit specific data processing tasks to the computer server system 164 and receive dynamic updates to the home data 202 and the derived home data 208. For example, a fire department or fire monitoring service provider can develop applications using the APIs 210 to provide emergency response services to users.

In other embodiments, the services 204 can utilize third-party APIs to communicate with third-party applications. For example, if a smart hazard detector is triggered, a hazard event can be transmitted to an emergency response system, such as one provided by a fire department, using an API of the emergency response system. Third-party APIs can also be used to collect user data and user activity data from third-parties. For example, an API of a social network provider can be utilized to gather user activity data for a user.

Figure 3:
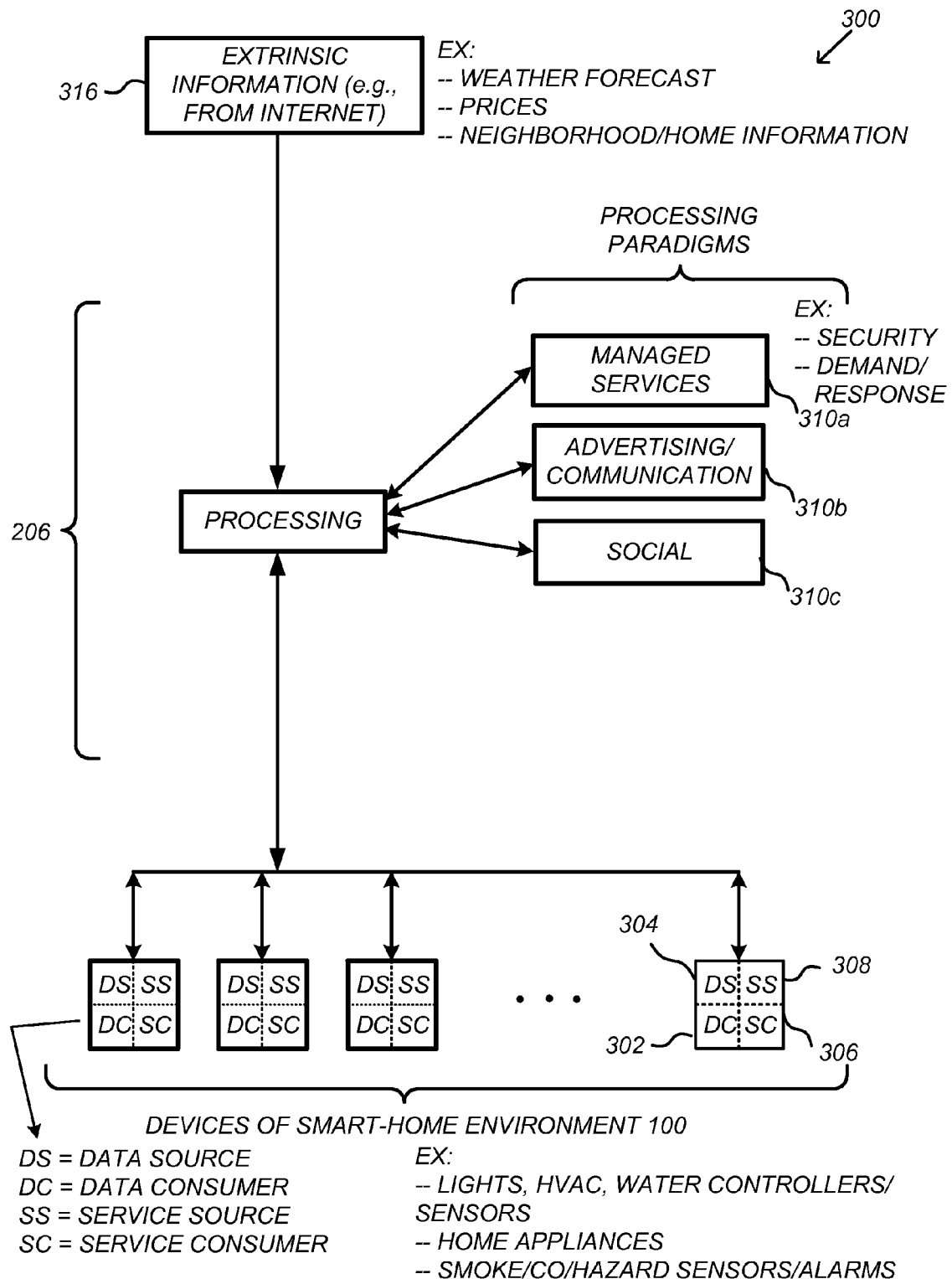
FIG. 3 is an abstracted functional view of one embodiment of a system for providing a pre-alarm of a developing hazardous condition.

FIG. 3 is an abstracted functional view of one embodiment of a system 300 for providing a pre-alarm of a developing hazardous condition. Smart devices, such as those of the smart-home environment 100 of FIG. 1, share common characteristics in that each smart device is a data consumer 302 (DC), a data source 304 (DS), a services consumer 306 (SC), and a services source 308 (SS). System 300 can be configured to harness the large amount of data generated by the smart devices to provide a variety of automated, extensible, flexible, and/or scalable technologies for achieving useful objectives. These objectives may be predefined or adaptively identified based on, e.g., user activity data or user input.

System 300 includes processing engine 206, which further includes a number of paradigms 310. Processing engine 206 can include a managed services paradigm 310a that monitors and manages device functions, such as ensuring proper operation of a device, responding to emergency situations, or detecting failure of equipment coupled to the device (e.g., a burned out light bulb). Processing engine 206 can further include an advertising/communication paradigm 310b that identifies characteristics (e.g., demographic information) of a user or products of interest to a user based on device usage. Processing engine 206 can further include a social paradigm 310c that collects data from and transmits data to a social network. For example, a user's status as reported on the social network can be collected and processed to determine user activity.

The processing engine 206 can also utilize extrinsic information 316 with the processing paradigms. Extrinsic information 316 can be used to interpret data received from a smart device, to determine a characteristic of the environment near the smart device (e.g., outside an enclosure that contains the smart device), to determine services or products available to the user, to identify a social network or social-network information, to determine contact information of entities (e.g., public service entities such as an emergency response team, the police or a hospital) near the smart device, or to identify statistical or environmental conditions, trends or other information associated with a home or neighborhood.

Figure 4:
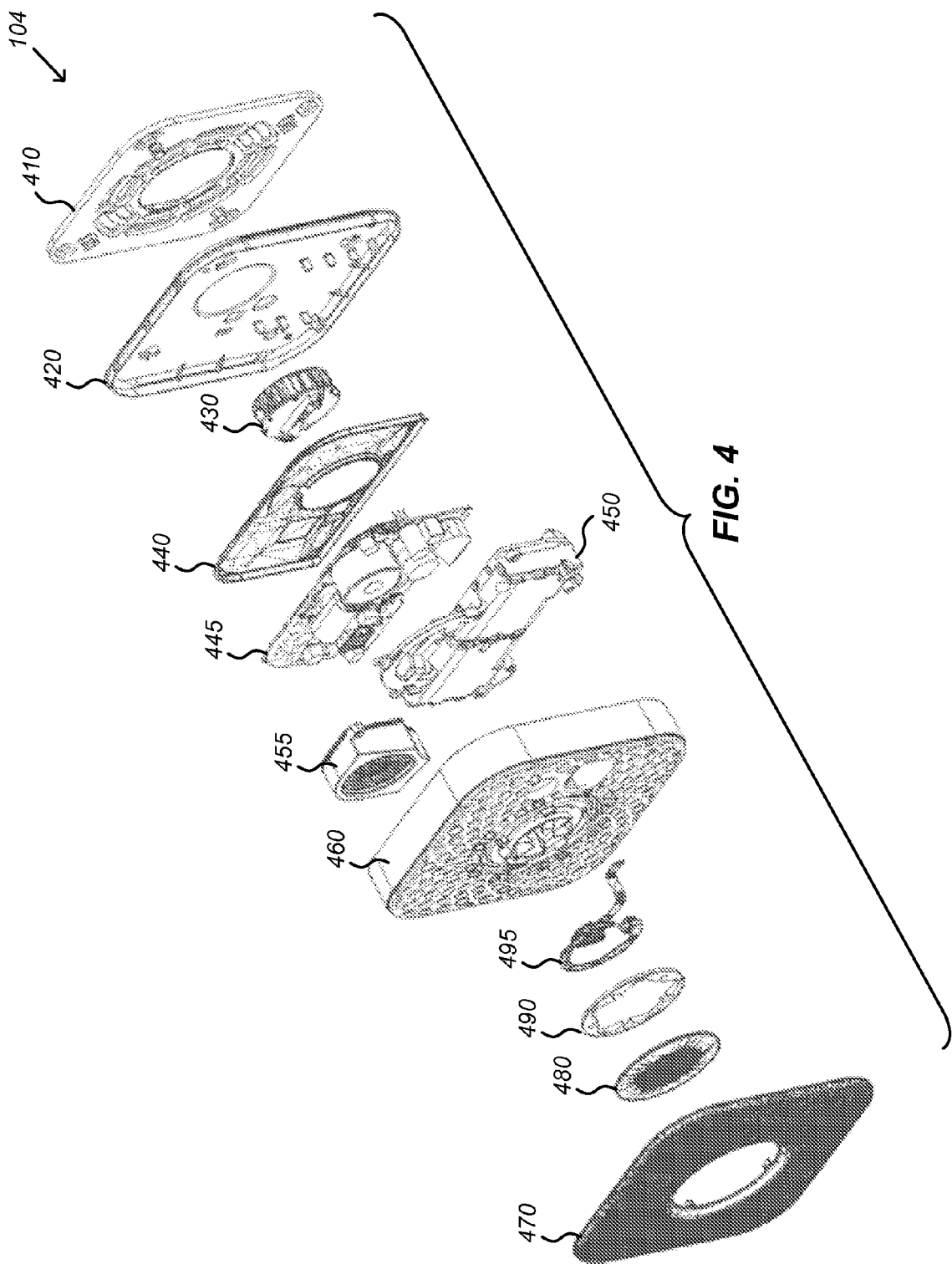
FIG. 4 is an illustration of an exploded perspective view of a smart hazard detector for providing a pre-alarm of a developing hazardous condition.

FIG. 4 is an illustration of an exploded perspective view of a smart hazard detector 104 for providing a pre-alarm of a developing hazardous condition. Hazard detector 104 can include a smoke detector, carbon monoxide detector, heat detector, and humidity sensor. Hazard detector 104 is configured to sound an audible notification, such as an alarm, when a sufficient level (e.g., above a threshold setting) of smoke or some other hazardous substance is detected. In one embodiment, hazard detector 104 also includes other sensors such as a motion sensor or ambient light sensor. Hazard detector 104 can also include a wireless transceiver for transmitting data, e.g., when a hazardous substance or user activity is detected, to other smart devices or a computer server system.

In one embodiment, hazard detector 104 is a roughly square or rectangular shaped object having a width of approximately 120 to 134 mm and a thickness of approximately 38 mm. Hazard detector 104 includes a mounting plate 410 that can be attached to a wall or ceiling and a back plate 420 that can be mounted to the mounting plate 410. Hazard detector 104 further includes a front casing 460 that can be secured to the back plate 420 to define a housing with an interior region for containing the components of the hazard detector 104.

A circuit board 445 can be attached to the back plate 420 and various components can be mounted to the circuit board 445. For example, a smoke chamber 430 can be mounted on circuit board 445 and configured to detect the presence of smoke. In one embodiment, smoke chamber 430 can be mid-mounted relative to circuit board 445 so that air can flow into smoke chamber 430 from above the circuit board 445 and below the circuit board 445. A speaker 455 and alarm device (not numbered), such as a horn, can also be mounted on circuit board 445 to audibly warn an occupant of a potential fire danger when the presence of smoke is detected in the smoke chamber 430. Other components, such as a motion sensor (e.g., ultrasonic, passive IR, etc.), carbon monoxide sensor, temperature sensor, heat sensor, ambient light sensor, noise sensor, one or more microprocessors, and the like may likewise be mounted on circuit board 445.

In one embodiment, a protective plate 440 can be attached to circuit board 445 to provide a visually pleasing appearance to the inner components of hazard detector 104 or to funnel airflow to smoke chamber 430. For example, when a user views the internal components of hazard detector 104, such as through the vents in back plate 420, protective plate 440 can provide the appearance of a relatively smooth surface and otherwise hide the components or circuitry of circuit board 445. Protective plate 440 can likewise function to direct air flow from the vents of back plate 420 toward smoke chamber 430.

Hazard detector 104 can also include a battery pack 450, which can be the main source of power for the various components of hazard detector 104. In one embodiment, battery pack 450 is a backup power source and hazard detector 104 is further coupled with a primary external power source, such as a 120 V power source of the home or enclosure. In some embodiments, a cover plate 470 can be attached to the front casing 460 to provide a visually pleasing appearance or for other functional purposes. In a specific embodiment, cover plate 470 may include a plurality of holes or openings so that the sensors on circuit board 445 can detect external objects. The plurality of openings can be arranged to provide a visually pleasing appearance when viewed. For example, the openings can be arranged according to a repeating pattern, such as a Fibonacci or other sequence.

A lens button 480 can be coupled with or otherwise mounted to cover plate 470. Lens button 480 can be transparent, allowing the sensors to view through the lens button 480. For example, a PIR sensor (not shown) can be positioned behind the lens button 480 to detect the activity or movement of a user. In some embodiments, lens button 480 can also function as a pressable button for inputting commands, such as to shut off a false alarm. A light ring 490 can be positioned distally behind lens button 480. The light ring 490 can be configured to receive and disperse light, e.g., from an LED or other light source, so as to provide a desired visual appearance, such as a halo, behind the lens button 480. A flexible circuit board 495 that includes one or more electrical components, such as a PIR sensor or LEDs, can be positioned behind the light ring 490. Flexible circuit board 495 can be electrically coupled to circuit board 445, enabling data communications with one or more microprocessors mounted on circuit board 445.

Figure 5:
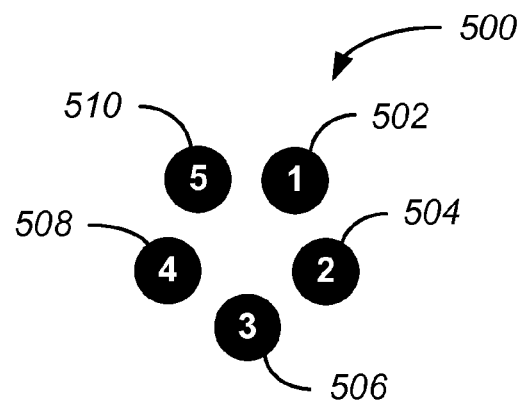
FIG. 5 is an illustration of the arrangement pattern of LED lights on a hazard detector, according to an embodiment.

FIG. 5 is an illustration of the arrangement pattern of LED lights on a hazard detector, according to an embodiment. This representation includes five light elements 502, 504, 506, 508 and 510. Light elements 500 may be turned on and off according to a number of patterns and each may cycle through different hue ranges. The color of each light element may also vary in order to provide an additional variety of visual effects. In one embodiment, light elements 500 can generate light in at least three colors: a first color, a second color, and a third color. The second color is between the first color and the third color on the color spectrum. For example, the first color can be green, the second color can be yellow, and the third color can be red.

Figure 6:
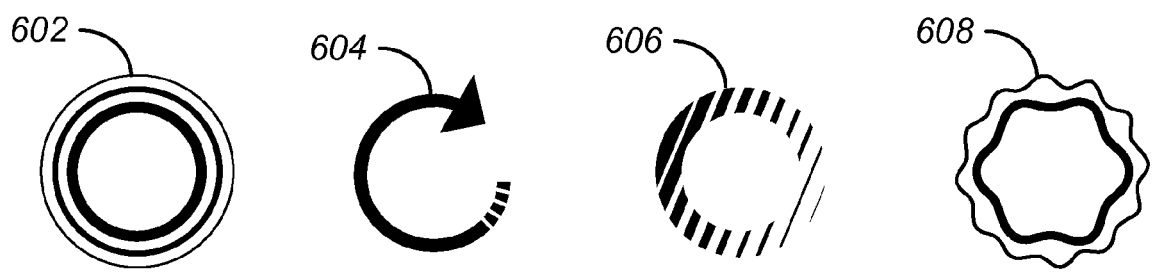
FIG. 6 is an illustration representing four different visual effects that can be generated by a hazard detector, according to an embodiment.

FIG. 6 is an illustration representing four different visual effects that can be generated by a hazard detector, according to an embodiment. Visual effect 602 is a representation of a pulsing effect that may be created when all of lights elements 502, 504, 506, 508 and 510 (shown in FIG. 5) are turned on and off simultaneously. Alternatively, all of light elements 502, 504, 506, 508 and 510 may increase and decrease the brightness of the light produced in a synchronized fashion to create a pulsing effect.

Visual effect 604 represents a rotating effect that can be created when all of light elements 502, 504, 506, 508 and 510 are turned on and off sequentially in a clockwise direction. In one embodiment, turning on and off the lights can be done in a gradual fashion. For example, light element 504 can gradually turn off and light element 502 gradually turns on while light elements 506, 508 and 510 are turned on at an equal brightness.

Visual effect 608 represents a wave visual effect that can be created when light elements 500 (shown in FIG. 5) turn on and off in a side-to-side direction. For example, at a given point in time, light element 510 is the brightest, light elements 508 and 502 are the next brightest, and light elements 506 and 504 are the least bright. Shortly thereafter, the lights may gradually change brightness in a linear manner such that light elements 504 and 506 are the brightest, lights 508 and 502 are the next brightest, and light 510 is the least bright.

Visual effect 610 represents a shimmer visual effect that can be created when each of the light elements 500 cycle through a hue range pattern, with each light element's hue range pattern being out of sync with all the other lights.

Figure 7:
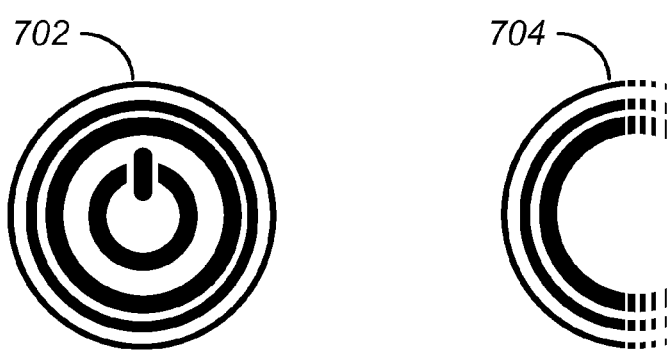
FIG. 7 is an illustration representing variations of a pulse visual effect that can be generated by a hazard detector, according to an embodiment.

FIG. 7 is an illustration representing variations of a pulse visual effect that can be generated by a hazard detector, according to an embodiment. Visual effect 702 represents an on and off pattern for power off or no power available situations wherein the pulse animations will transition smoothly through pulses in order to provide an alert in a non-distracting manner. Visual effect 704 represents a left-to-right pulse pattern that could be used when presenting a user with selectable options via visual effects. For example, a button can be used to select a language preference for the operation of a hazard detector during initial setup. The user can be asked to press the button when the left side is pulsing for English and when the right side is pulsing for Chinese.

Figure 8:
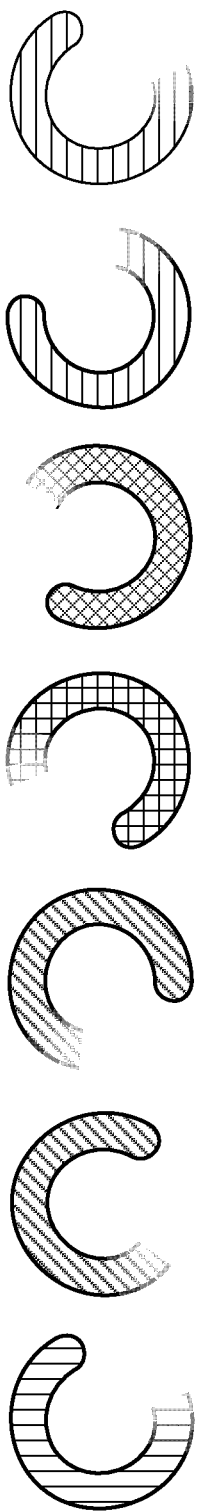
FIG. 8 is an illustration of a rotating visual effect that can be generated by a hazard detector, according to an embodiment.

FIG. 8 is an illustration of a rotating visual effect that can be generated by a hazard detector, according to an embodiment. FIG. 8 provides a further illustration of the rotating visual effect 604 of FIG. 6. Viewed from left to right, FIG. 8 shows new lights turning on at one end of the rotating visual effect and other lights gradually turning off at the other end of the rotating visual effect. The hatch patterns of each of the sequential representations illustrate how the rotating light may change color during the rotation sequence. Although light elements 502, 504, 506, 508 and 510 may each be a different color individually, the colored light mixing causes the color of the rotating visual effect to constantly change during the course of the visual effect.

Figure 9:
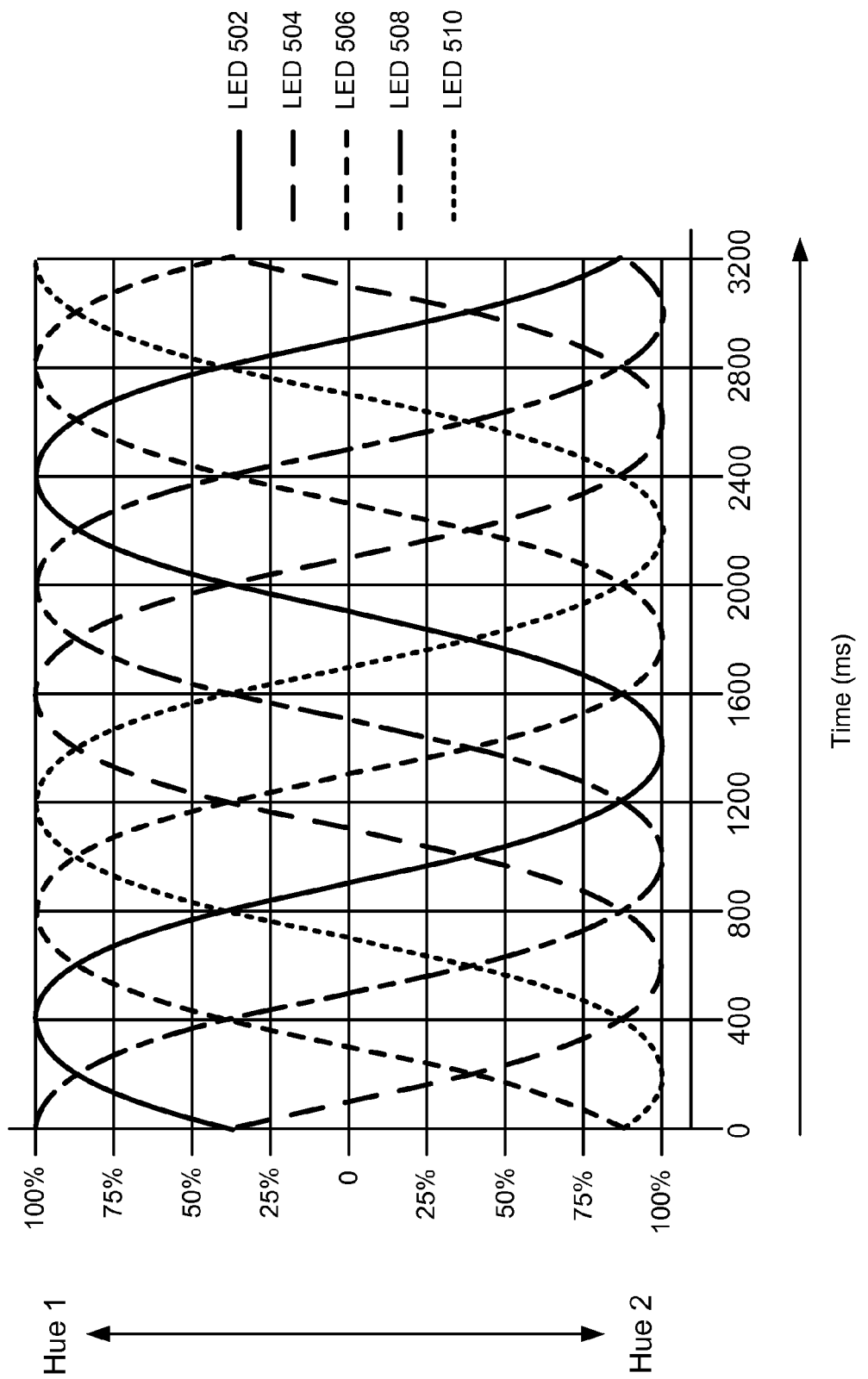
FIG. 9 is an illustration of the different hue range patterns associated with each of the light elements for a shimmering visual effect that can be generated by a hazard detector, according to an embodiment.

FIG. 9 is an illustration of the different hue range patterns associated with each light element for a shimmering visual effect that can be generated by a hazard detector, according to an embodiment. The extent to which the lights 502, 504, 506, 508 and 510 are out of sync may be varied in order to produce variations of the shimmering visual effect.

In various embodiments, the visual effects described above can be varied in a number of different ways. For example, each effect may be animated faster or slower, brighter or dimmer, for a specific number of animation cycles, with only some of the light participating, and using different colors, e.g., white, blue, green, yellow and red. These visual effects can be generated by a hazard detector for a variety of purposes. For example, a specific color, animation, animation speed, etc. or combinations thereof can represent one or more of the following alerts or notifications provided by a hazard detector: booting up, selecting language, ready for connections, connected to client, button pressed, button pressed for test, countdown to test, test under way, test completed, pre-alarms or Heads Up notifications, smoke alarms, carbon monoxide alarms, heat alarms, multi-criteria alarms, hushed after alarm, post-alarm, problems, night light state, reset, shutdown begin, shutdown, safely light, battery very low, battery critical, power confirmation, and more.

Figure 10:
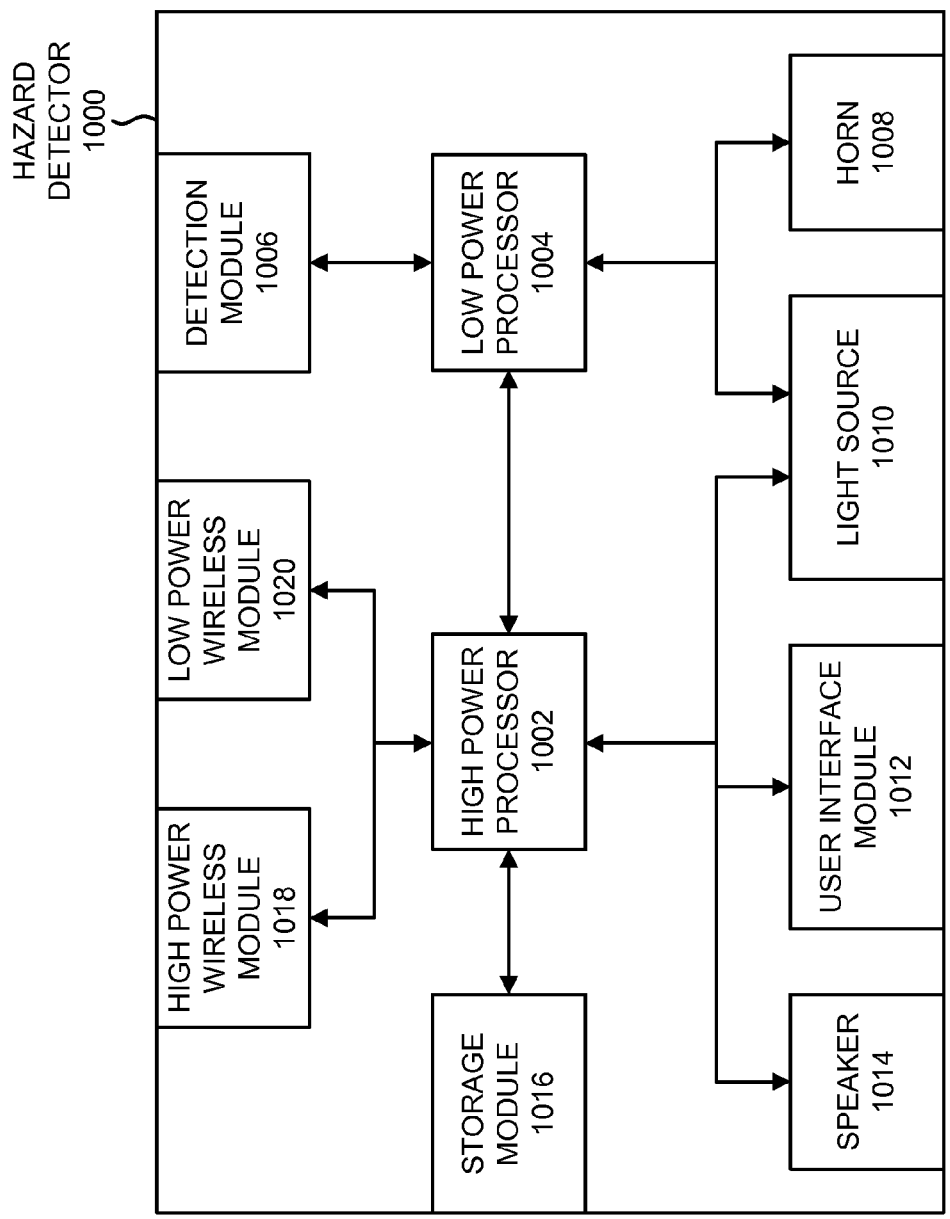
FIG. 10 is a block diagram of an embodiment of a hazard detector for providing a pre-alarm of a developing hazardous condition.

FIG. 10 is a block diagram of an embodiment of a hazard detector 1000 for providing a pre-alarm of a developing hazardous condition. Hazard detector 1000 includes a high power processor 1002, a low power processor 1004, a detection module 1006, a horn 1008, a light source 1010, a user interface module 1012, a speaker 1014, a storage module 1016, a high power wireless module 1018, and a low power wireless module 1020.

According to this preferred embodiment, a bifurcated or hybrid processor circuit topology is used for handling various features of the hazard detector 1000. Low power processor 1004 is a relatively small processor that is dedicated to core hazard detection and alarming functionality as would be provided in a conventional hazard detector. High power processor 1002 is a relatively large processor that consumes more power than low power processor 1004 and handles more advanced features such as cloud communications, user interface features, occupancy and other environmental tracking features, and more generally any other task that would not be considered a "core" or "conventional" detection and alarming task.

By way of example and not by way of limitation, low power processor 1004 can be a Freescale KL 15 microcontroller, while high power processor 1002 can be a Freescale K60 microcontroller. High power processor 1002 is designed to interoperate with and is coupled to low power processor 1004. Low power processor 1004 is configured to perform its core safety-related functions regardless of the status or state of high power processor 1002. Thus, even if high power processor 1002 is not available, low power processor 1004 will continue to perform its core functions to ensure that hazard detector 1000 meets all industry and/or government safety standards.

Low power processor 1004 is coupled to detection module 1006, horn 1008, and light source 1010. Detection module 1006 includes safety sensors, such as smoke and CO sensors. Low power processor 1004 can poll detection module 1006 and activate horn 1008 to generate an alarm sound when one or more of safety sensors detect a level of hazardous substance that is greater than or equal to an emergency threshold. Low power processor 1004 can also activate light source 1010 in a specific color, such as red, when a hazardous substance is detected.

High power processor 1002 is coupled to speaker 1014 and light source 1010. High power processor 1002 can also receive readings from detection module 1006 via low power processor 1004. In other embodiments, high power processor 1002 is also coupled to detection module 1006 and can receive readings directly. If a detected hazard level is less than the emergency threshold, high power processor 1002 can check if the detected hazard level is greater than or equal to a pre-alarm threshold. If the detected hazard level is greater than or equal to the pre-alarm threshold, high power processor 1002 can activate speaker 1014 to generate speech that warns of the developing hazardous condition. High power processor 1002 can also activate light source 1010 in a different color than when emergency levels of hazardous substance is detected. For example, light source 1010 can be activated in a yellow color if the detected hazard level is greater than or equal to the pre-alarm threshold but less than the emergency threshold.

High power processor 1002 is also coupled to high power wireless module 1018 and low power wireless module 1020. In one embodiment, high power wireless module 1018 communicates wirelessly with a router or gateway of a local area network. The router or gateway also provides internet access, and high power processor 1002 can use high power wireless module 1018 to transmit a hazard event or some other form of notification to a computer server system if emergency or pre-alarm levels of hazardous substance is detected. The computer server system can then transmit the notification to a user's computer or mobile device. Low power wireless module 1020 communicates directly with other smart devices via a personal area mesh network. High power processor 1002 can use low power wireless module 1020 to transmit signals to other smart devices when a hazardous substance is detected, and the other devices can also generate alarms or pre-alarms depending on the detected hazard level.

High power processor 1002 is further coupled to user interface module 1012, which can include motion sensors, audio sensors, cameras, and buttons. User interface module 1012 receives input from a user, which can be in the form of a specific motion, a phrase or sound, or a button press. The user input is transmitted to high power processor 1002, which can then determine which actions need to be taken in response to the user input. For example, the user can perform a specific motion, such as waving of the hands, or press a button to shut off an alarm generated by horn 1008 or a pre-alarm generated by speaker 1014. In one embodiment, only the hazard detector that detected the hazardous substance can receive user input to shut off the alarm or pre-alarm. Thus, if the user tries to press the button or perform the motion in front of a hazard detector that activated the alarm or pre-alarm in response to receiving a signal from another hazard detector, the alarm or pre-alarm will continue to sound.

Storage module 1016 is coupled to high power processor 1002 and can be used to store the emergency and pre-alarm threshold settings. Storage module 1016 can also be coupled to low power processor 1004 so that low power processor 1004 can retrieve the threshold settings directly. In some embodiments, hazard detector 1000 further includes heat and humidity sensors that are coupled to high power processor 1002. High power processor 1002 can adjust the threshold settings based on readings from the heat and humidity sensors. For example, if the heat sensor detects a rate of temperature increase that is greater than a threshold, high power processor 1002 can decrease the pre-alarm or emergency threshold for smoke since fast rising temperatures can indicate fire. If the humidity sensor detects a rise in humidity that is greater than a threshold, high power processor 1002 can increase the pre-alarm or emergency threshold for smoke since rising humidity can indicate steam, which causes false alarms.

Figure 11:
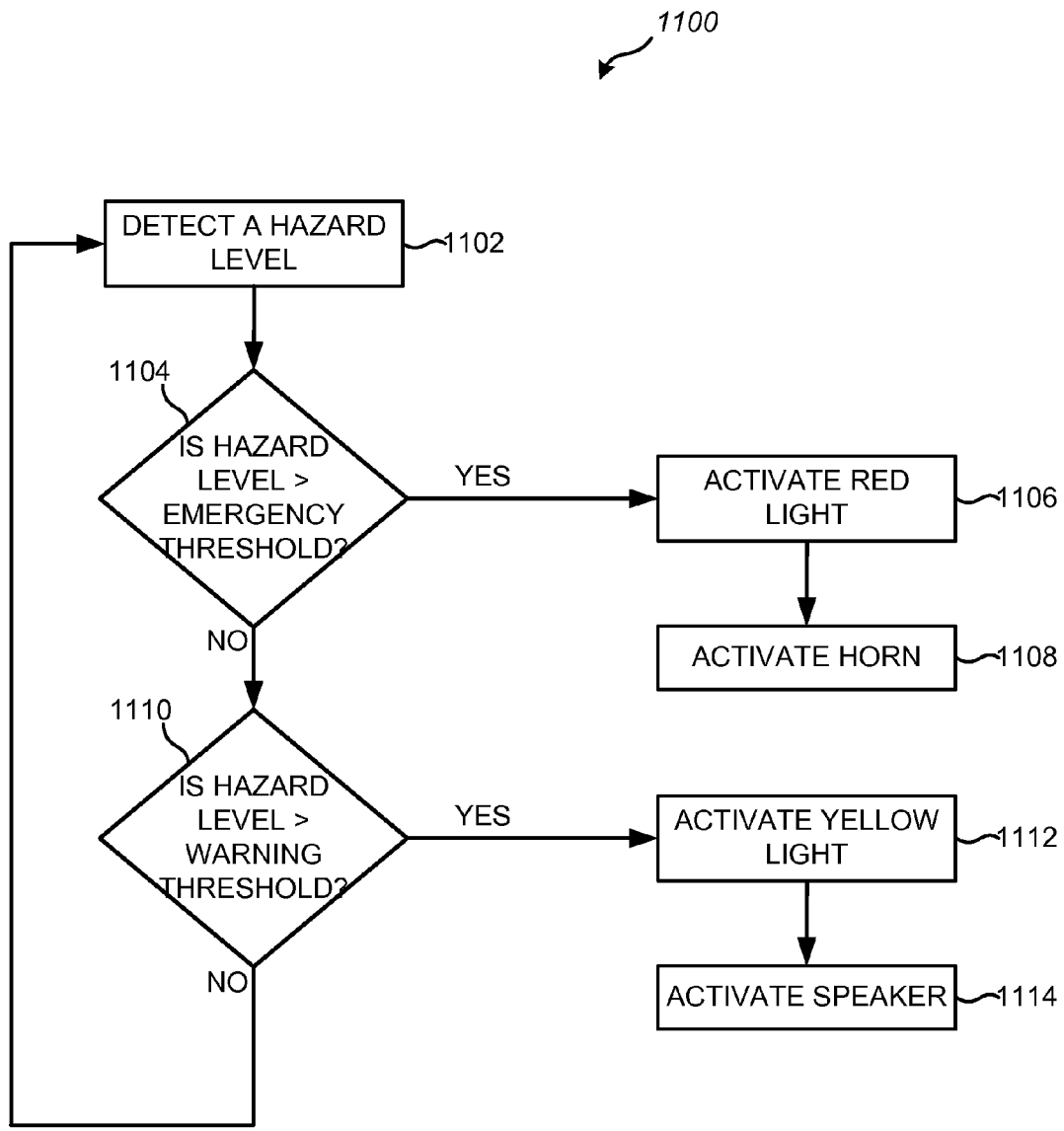
FIG. 11 is a flowchart of one embodiment of a process for providing a pre-alarm of a developing hazardous condition.

FIG. 11 is a flowchart of one embodiment of a process 1100 for providing a pre-alarm of a developing hazardous condition. Process 1100 can be performed by a smart hazard detector such as the one described herein above with respect to FIG. 10. Process 1100 starts at block 1102 when a hazard level is detected. At block 1104, it is determined whether the hazard level is greater than an emergency threshold. If the hazard level is greater than the emergency threshold, a red light is activated at block 1106 and the horn is activated to generate an alarm at block 1108.

Referring back to block 1104, if the detected hazard level is not greater than the emergency threshold, process 1100 goes to block 1110 to determine if the hazard level is greater than a pre-alarm threshold. If the hazard level is not greater than the pre-alarm threshold, process 1100 goes back to block 1102 to repeat the process. If the hazard level is greater than the pre-alarm threshold, a yellow light is activated at block 1112. In other embodiments, a spatiotemporal pattern or any of the visual effects described herein above with respect to FIGS. 5-9 can also be generated by the yellow light. For example, a pulsing effect can be generated by modulating the light source that is generating the yellow light.

At block 1114, the speaker is activated if the detected hazard level is greater than the pre-alarm threshold. The speaker generates sounds at a lower volume than the horn and can generate a variety of different sounds and sound patterns. In one embodiment, the speaker generates a sound pattern with a lower pitch or frequency than an alarm. For example, a bell or chime sound can be generated. In other embodiments, the speaker generates a pre-alarm speech that announces the developing hazardous condition. The speech can also include content such as the type of hazardous substance that was detected, the location that it was detected at, which can be the name of a room in a house or enclosure, and a warning that the alarm may sound. For example, the speech can say: "Heads up. There is smoke in the kitchen. The horn may sound." In one embodiment, the light source pulses in synchronization with the speech. For example, the light source can be modulated such that the generated light is bright when a syllable or word is announced by the speaker and the light is dim or off between syllables or words.

In one embodiment, the light and the speaker also provides notifications for when the hazardous substance is no longer detected. For example, the light source can be activated in a green color and the speaker can generate speech that says: "Smoke has cleared in the kitchen." In another embodiment, pre-alarm notifications can also be generated when the hazard detector's battery life is low. For example, if the battery has less than six months of life remaining or if the battery charge is below a certain threshold, such as 25%, the users can be informed by a yellow light and/or the speaker generating speech that indicates the battery is low and should be replaced.

In further embodiments, pre-alarm notifications are also generated for other potential threats, such as security or structural integrity threats. For example, other smart devices or sensors in the home can detect indicators of the threats and transmit a signal to the hazard detector that causes the hazard detector to generate the pre-alarm. A pre-alarm notification associated with a structural integrity threat can say: "Heads up, water has been detected on the basement floor." Further examples of potential security or structural integrity threats include, by way of example, that it is past 7 PM and not all of the kids are home yet, that a large parcel has been left on the doorstep, that a current network intrusion has been detected at the family gaming computer, or any of a variety of other predetermined potential security or structural integrity threats for which a trigger, conclusion, or inference can be established.

Figure 12:
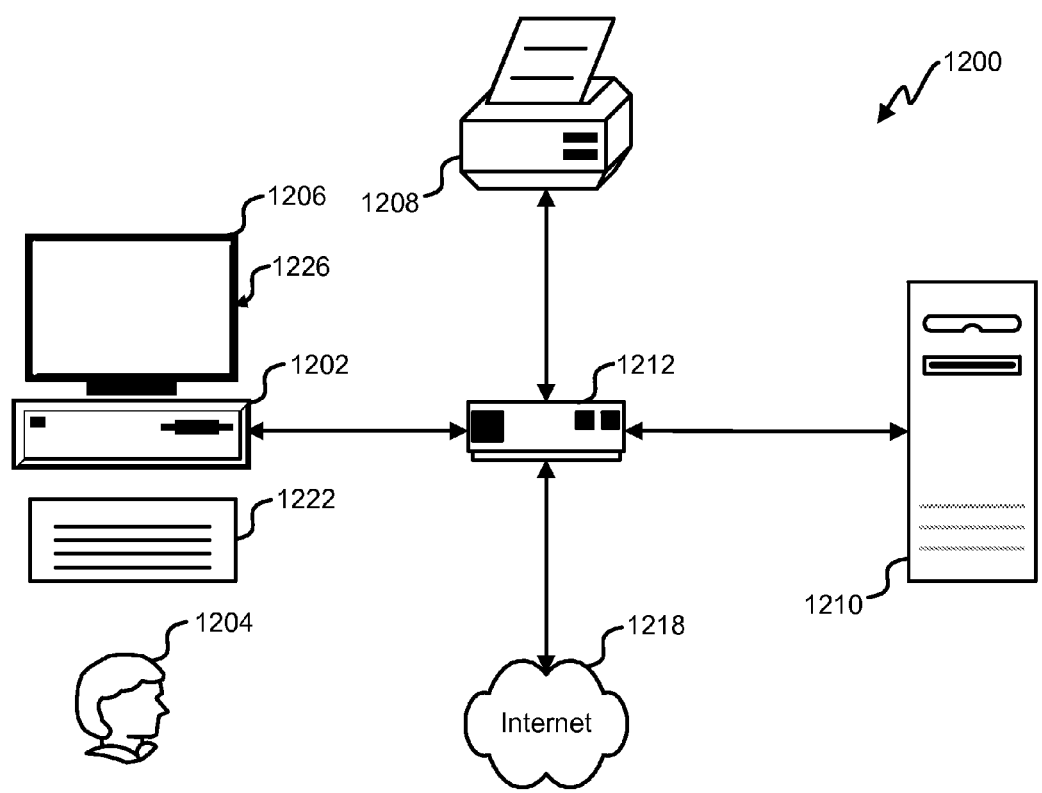
FIG. 12 is a block diagram of an exemplary environment for implementing one embodiment of a system for providing a pre-alarm of a developing hazardous condition.

FIG. 12 is a block diagram of an exemplary environment for implementing one embodiment of a system for providing a pre-alarm of a developing hazardous condition. The exemplary environment includes a computer system 1200 that can be used by a user 1204 to remotely control, for example, one or more of the smart devices according to one or more of the embodiments described herein. The computer system 1200 can alternatively be used for carrying out one or more of the server-based processing described herein above or as a processing device in a larger distributed computer server system for carrying out processing. The computer system 1200 can include a computer 1202, keyboard 1222, a network router 1212, a printer 1208, and a monitor 1206. The monitor 1206, processor 1202 and keyboard 1222 are part of a computer system 1226, which can be a laptop computer, desktop computer, handheld computer, mainframe computer, etc. The monitor 1206 can be a CRT, flat screen, etc.

A user 1204 can input commands into the computer 1202 using various input devices, such as a mouse, keyboard 1222, track ball, touch screen, etc. If the computer system 1200 comprises a mainframe, a designer 1204 can access the computer 1202 using, for example, a terminal or terminal interface. Additionally, the computer system 1226 may be connected to a printer 1208 and a server 1210 using a network router 1212, which may connect to the Internet 1218 or a WAN. While only one server 1210 is shown in the figure, it is understood that computer system 1226 can be connected to any number of servers.

The server 1210 may be used to store additional software programs and data. In one embodiment, software implementing the systems and methods described herein can be stored on a storage medium in the server 1210. Thus, the software can be run from the storage medium in the server 1210. In another embodiment, software implementing the systems and methods described herein can be stored on a storage medium in the computer 1202. Thus, the software can be run from the storage medium in the computer system 1226. Therefore, in this embodiment, the software can be used whether or not computer 1202 is connected to network router 1212. Printer 1208 may be connected directly to computer 1202, in which case, the computer system 1226 can print whether or not it is connected to network router 1212.

Figure 13:
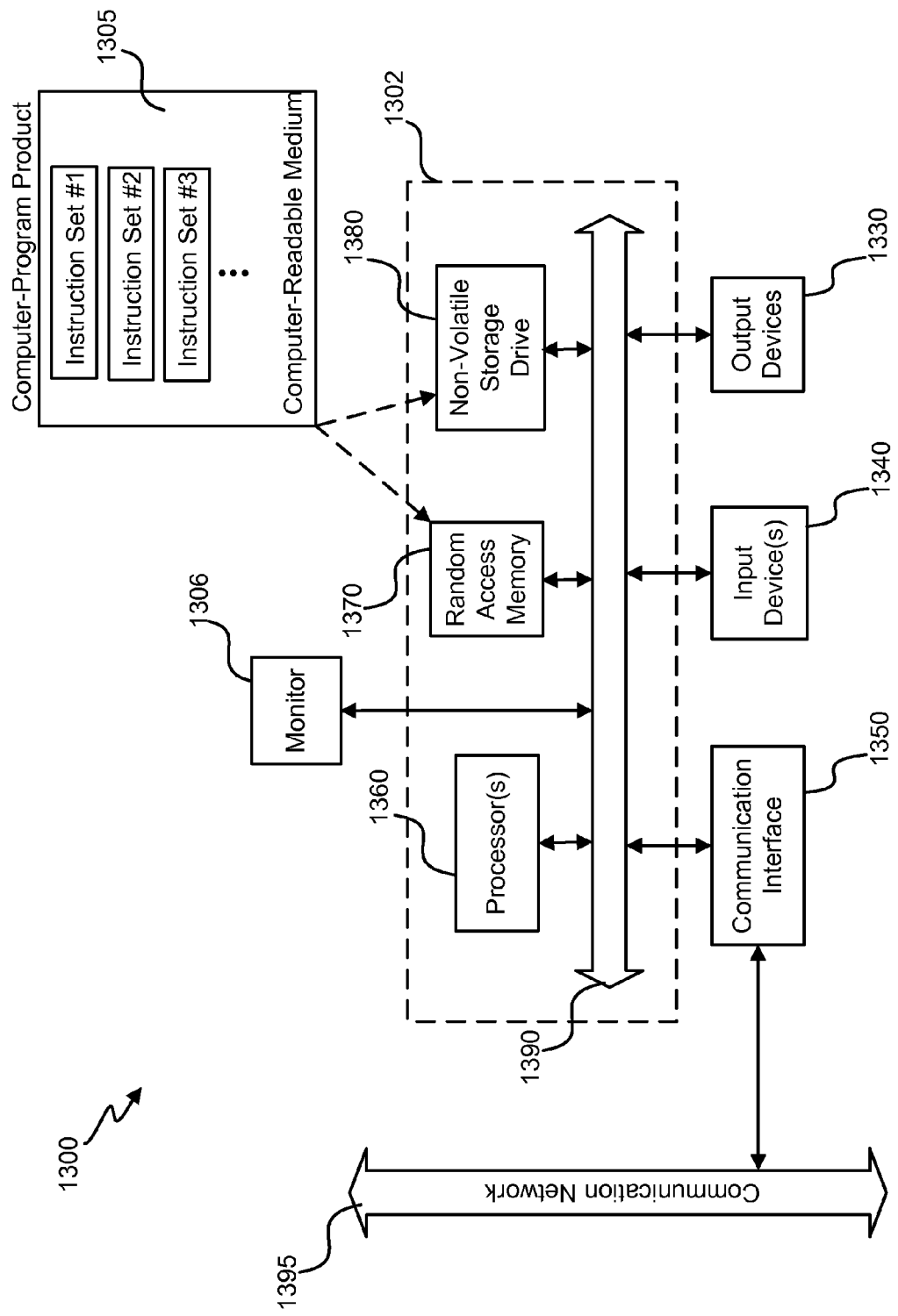
FIG. 13 is a block diagram of an embodiment of a special-purpose computer system for providing a pre-alarm of a developing hazardous condition.
Figure 17:
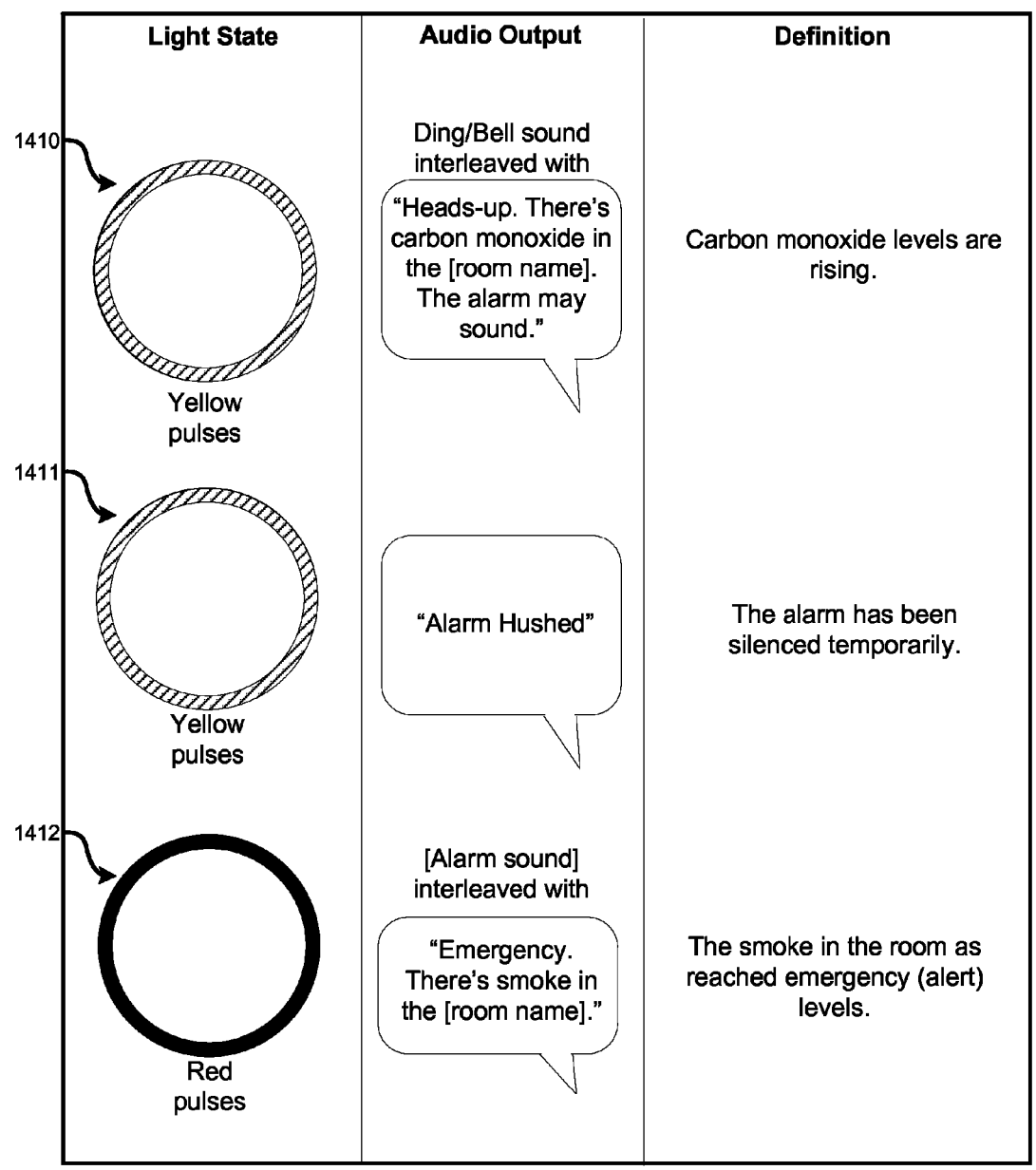
Figure 18:
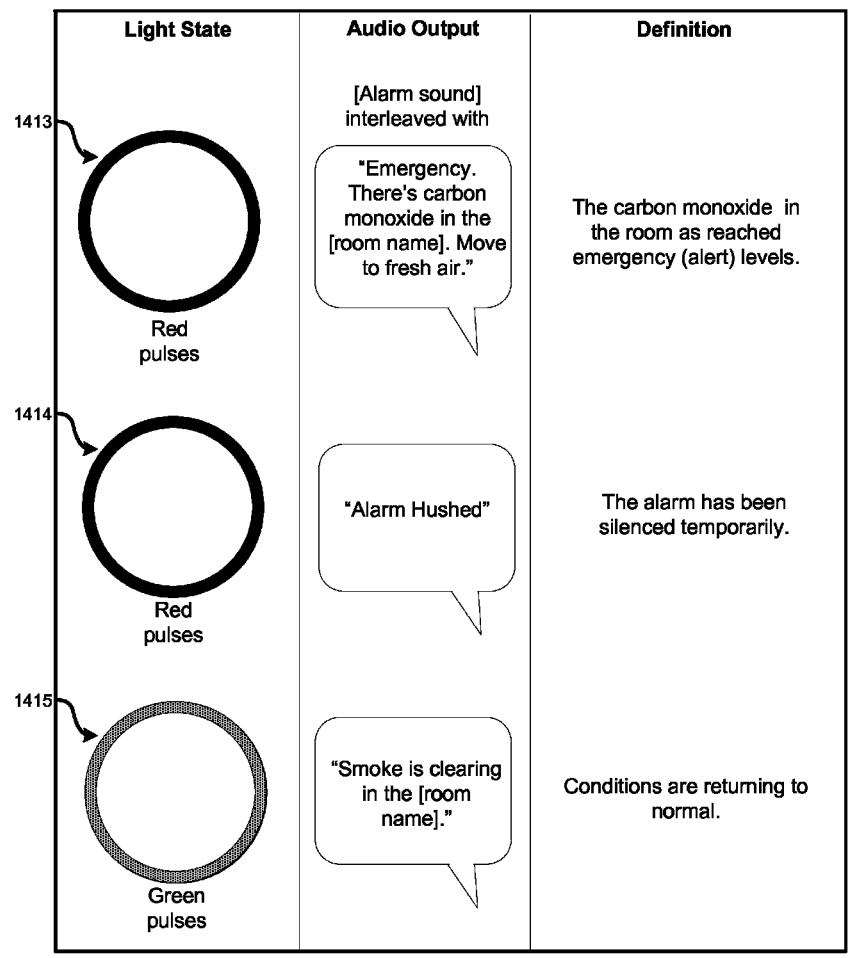

FIG. 13 is a block diagram of an embodiment of a special-purpose computer system 1300 for providing a pre-alarm of a developing hazardous condition. The methods and systems described herein may be implemented by computer-program products that direct a computer system to perform the actions of the methods and components. Each such computer-program product may comprise sets of instructions (codes) embodied on a computer-readable medium that directs the processor of a computer system to perform corresponding actions. The instructions may be configured to run in sequential order, or in parallel (such as under different processing threads), or in a combination thereof.

Special-purpose computer system 1300 comprises a computer 1302, a monitor 1306 coupled to computer 1302, one or more additional user output devices 1330 (optional) coupled to computer 1302, one or more user input devices 1340 (e.g., keyboard, mouse, track ball, touch screen) coupled to computer 1302, an optional communications interface 1350 coupled to computer 1302, a computer-program product 1305 stored in a tangible computer-readable memory in computer 1302. Computer-program product 1305 directs system 1300 to perform the above-described methods. Computer 1302 may include one or more processors 1360 that communicate with a number of peripheral devices via a bus subsystem 1390. These peripheral devices may include user output device(s) 1330, user input device(s) 1340, communications interface 1350, and a storage subsystem, such as random access memory (RAM) 1370 and non-transitory storage drive 1380 (e.g., disk drive, optical drive, solid state drive), which are forms of tangible computer-readable memory.

Computer-program product 1305 may be stored in non-transitory storage drive 1380 or another computer-readable medium accessible to computer 1302 and loaded into memory 1370. Each processor 1360 may comprise a microprocessor, such as a microprocessor from Intel® or Advanced Micro Devices, Inc.®, or the like. To support computer-program product 1305, the computer 1302 runs an operating system that handles the communications of product 1305 with the above-noted components, as well as the communications between the above-noted components in support of the computer-program product 1305. Exemplary operating systems include Windows® or the like from Microsoft Corporation, Solaris® from Sun Microsystems, LINUX, UNIX, and the like.

User input devices 1340 include all possible types of devices and mechanisms to input information to computer system 1302. These may include a keyboard, a keypad, a mouse, a scanner, a digital drawing pad, a touch screen incorporated into the display, audio input devices such as voice recognition systems, microphones, and other types of input devices. In various embodiments, user input devices 1340 are typically embodied as a computer mouse, a trackball, a track pad, a joystick, wireless remote, a drawing tablet, a voice command system. User input devices 1340 typically allow a user to select objects, icons, text and the like that appear on the monitor 1306 via a command such as a click of a button or the like. User output devices 1330 include all possible types of devices and mechanisms to output information from computer 1302. These may include a display (e.g., monitor 1306), printers, non-visual displays such as audio output devices, etc.

Communications interface 1350 provides an interface to other communication networks and devices and may serve as an interface to receive data from and transmit data to other systems, WANs and/or the Internet 1218. Embodiments of communications interface 1350 typically include an Ethernet card, a modem (telephone, satellite, cable, ISDN), a (asynchronous) digital subscriber line (DSL) unit, a FireWire® interface, a USB® interface, a wireless network adapter, and the like. For example, communications interface 1350 may be coupled to a computer network, to a FireWire® bus, or the like. In other embodiments, communications interface 1350 may be physically integrated on the motherboard of computer 1302, and/or may be a software program, or the like.

RAM 1370 and non-transitory storage drive 1380 are examples of tangible computer-readable media configured to store data such as computer-program product embodiments of the present invention, including executable computer code, human-readable code, or the like. Other types of tangible computer-readable media include floppy disks, removable hard disks, optical storage media such as CD-ROMs, DVDs, bar codes, semiconductor memories such as flash memories, read-only-memories (ROMs), battery-backed volatile memories, networked storage devices, and the like. RAM 1370 and non-transitory storage drive 1380 may be configured to store the basic programming and data constructs that provide the functionality of various embodiments of the present invention, as described above.

Software instruction sets that provide the functionality of the present invention may be stored in RAM 1370 and non-transitory storage drive 1380. These instruction sets or code may be executed by the processor(s) 1360. RAM 1370 and non-transitory storage drive 1380 may also provide a repository to store data and data structures used in accordance with the present invention. RAM 1370 and non-transitory storage drive 1380 may include a number of memories including a main random access memory (RAM) to store instructions and data during program execution and a read-only memory (ROM) in which fixed instructions are stored. RAM 1370 and non-transitory storage drive 1380 may include a file storage subsystem providing persistent (non-transitory) storage of program and/or data files. RAM 1370 and non-transitory storage drive 1380 may also include removable storage systems, such as removable flash memory.

Bus subsystem 1390 provides a mechanism to allow the various components and subsystems of computer 1302 to communicate with each other as intended. Although bus subsystem 1390 is shown schematically as a single bus, alternative embodiments of the bus subsystem may utilize multiple busses or communication paths within the computer 1302.

FIGS. 14-20 represent various illumination states that may be output by a hazard detector, such as the hazard detectors and other smart-home devices detailed herein. Such illumination states may involve various colors and animations. Synthesized or recorded spoken audio messages may accompany at least some of such illumination states as detailed in the charts of FIGS. 14-20. The majority of the time, it can be expected that no light of a hazard detector will be illuminated. When the light is illuminated, the hazard detector is conveying a message (other than if light state 1403 is illuminated). States 1401 and 1402, which involve blue and green illumination, are illustrated in FIG. 14 and may be presented during a set up process. State 1403 involves a conditional illumination state, which can be referred to as a "path light" state. Such a state may be illuminated in response to motion and the brightness level in an ambient environment of a hazard detector dropping below a threshold brightness level. States 1404 and 1405 represent pre-alarm (pre-alert or early warning) states and emergency (alert or alarm) states. State 1406 may be for a separate light of the hazard detector that is indicative of if a wired (e.g., non-battery) power source is connected and available, such as a household's 140 V AC power supply. State 1407 may be used as part of a setup process. For instance, "[device]" may be replaced with a spoken indication of the brand name of the hazard detector. State 1408 may be presented when a user presses a button to test the hazard detector. State 1409 may represent a state that is indicative of a potential danger and may server as an early warning. For state 1409 (and other states having a similar designation), [room type] may be replaced with a spoken indication of the type of room in which the hazard detector is installed. At the time of installation, a user may have specified to the hazard detector, such as via a selection menu, the type of room in which the hazard detector was being installed. States 1410 and 1411 represent additional pre-alarm states. States 1412, 1413, and 1414 represent various alarm (alert) states. State 1415 may be output when a smoke hazard is clearing. State 1416 may be output when a carbon monoxide hazard is clearing. States 1417, 1418, 1419, 1420, 1421 represent states output in response to a status check that identifies a problem with the hazard detector. Such a state being output may require one or more user actions to resolve.

Preferably, the voice advisories during emergency-level alerts are interleaved in time during silent periods between loud, shrieking tonal alarm patterns, so as to comply with regulations such as National Fire Protection Association (NFPA) and Underwriters Laboratories (UL) standards that require a maximum silence period between tonal alarm patterns of 1.5 seconds (Ref UL2034, UL217, NFPA72 and NFPA720).

It should be understood that the above detailed illumination states and audio messages are merely exemplary. In various other embodiments, the colors, animations, definitions and/or audio messages may be modified.

In order to provide input to various embodiments of the hazard detectors detailed herein, it may be possible to perform a gesture to provide input, which may result in silencing "nuisance" alarms—that is, alarms triggered by a non-hazardous condition (e.g., burning toast). Within a distance of approximately 2-6 feet of the hazard detector, a wave of a user's hand and arm can be detected. In some embodiments, multiple waves must be performed for the gesture to be detected. As detailed in relation to FIG. 21, some of the pre-alert or alert states may silenced, at least temporarily, by using a wave gesture. In some situations, as noted in FIG. 21, certain situations preclude the alarm from being silenced. A wave gesture can also be used for canceling a manual test and/or to hear a detailed message when a visual status is being presented via illumination. In some embodiments, rather than performing a gesture, a user may push a button (or physically actuate some other part) of the hazard detector.

If multiple hazard detectors are present, all of the hazard detectors may output light and sound of a heads-up (pre-alert) or emergency (alert) situation is present. To silence an alarm (either in the pre-alert or alert state), the user may be required to perform the gesture (or push a button) at the hazard detector that originally detected the hazard. Once the proper hazard detector is silenced, each other hazard detector may be silenced (based on wireless communication between the hazard detectors).

Figure 22:
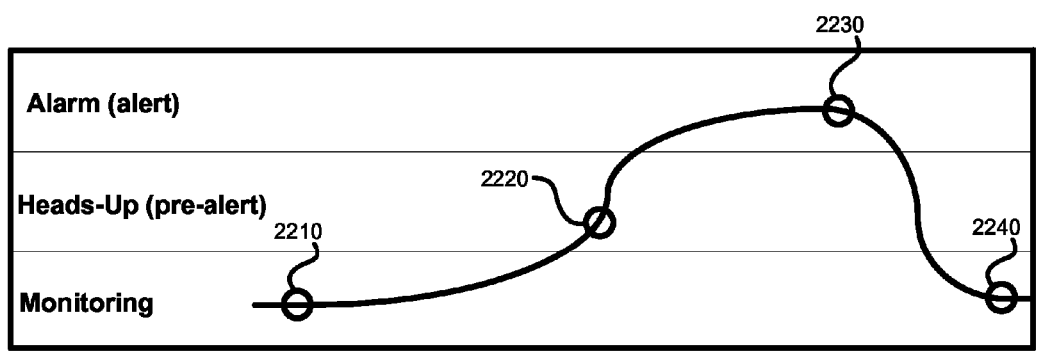
FIG. 22 illustrates an exemplary situation of when a heads-up (pre-alert) state is used prior to an alarm (emergency) state.

Referring to FIG. 22, an exemplary situation of when a heads-up (pre-alert) state is used. A gentle heads-up (pre-alert) warns a user of a condition that has risen above normal, but has not yet triggered a full alert (emergency) state. Sounds and messages output during a pre-alert state are intended to be less irritating and urgent than messages during an alert state. By having such a pre-alarm state, users may be less likely to disable a hazard detector and, thus, the hazard detector may be more likely to be functioning when needed.

As an example, at point 2210, the hazard detector is monitoring its ambient environment for hazards, such as smoke and carbon monoxide. An increased level of carbon monoxide or smoke may be detected at point 2220. At such point, a pre-alert message and illumination may be output to warn users of the impending conditions. Such a pre-alert may involve a notable, but non-jarring (in comparison to a shrieking emergency alarm sound), bell or ringing sound. The notable but non-jarring sound may be similar in intensity to the bell sound emitted by an elevator when arriving at the target floor, which is enough to notify but not so much as to unpleasantly jar the user. A user may be permitted to silence such a heads-up (pre-alert) message. At point 2230, a full alarm may be sounded, which may involve a loud, shrill alarm sound. At point 2240, a message (with an accompanying illumination state) may be output indicative of normal conditions resuming. Heads-up (pre-alert) states are associated with a yellow illumination state while emergency (alert) states are associated with red illumination states. If the hazard level in the environment of the hazard detector rises quickly, no pre-alert state may be entered by the hazard detector. Rather, the alarm state may be directly entered from a monitoring state.

It is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A hazard detector for providing a pre-alarm of a developing hazardous condition, the hazard detector comprising:
    a detection module configured to detect a hazard level, the hazard level indicating an amount of at least one of smoke and carbon monoxide (CO) present at the hazard detector;
    a storage module configured to store a pre-alarm threshold and an emergency threshold, the pre-alarm threshold being less than the emergency threshold;
    a light source configured to generate light in a first color, a second color, and a third color, the second color being between the first color and the third color on a color spectrum;
    a speaker configured to generate an audible sound;
    a user interface module in communication with the processing module, the user interface module being configured to receive user input;
    a horn configured to generate an audible alarm at a higher volume than the speaker; and
    a processing module coupled to the detection module, the storage module, the light source, the speaker, and the horn, the processing module being configured to:
        receive the detected hazard level from the detection module,
        compare the detected hazard level with the pre-alarm threshold,
        compare the detected hazard level with the emergency threshold,
        determine that the detected hazard level is greater than the pre-alarm threshold and less than the emergency threshold,
        generate an audible pre-alarm speech via the speaker in response to determining that the detected hazard level is greater than the pre-alarm threshold and less than the emergency threshold, the audible pre-alarm speech including content that warns of the developing hazardous condition,
        activate the light source in the second color in response to determining that the detected hazard level is greater than the pre-alarm threshold and less than the emergency threshold, receive the user input from the user interface module, and stop generating the audible pre-alarm speech in response to receiving the user input.

2. The hazard detector of claim 1, further comprising:

a high power wireless module coupled to the processing module, the high power wireless module being configured to transmit and receive data wirelessly via a local area network, wherein the processing module is further configured to transmit a hazard event to a computer server system via the high power wireless module, the hazard event indicating the detection of the hazard level that is greater than the pre-alarm threshold and less than the emergency threshold.

3. The hazard detector of claim 2, further comprising:

a low power wireless module coupled to the processing module, the low power wireless module being configured to transmit and receive data wirelessly via a personal area network at a slower rate of data transfer than the high power wireless module, and further configured to consume less power than the high power wireless module, wherein the processing module is further configured to transmit a signal to a second hazard detector via the low power wireless module in response to determining that the detected hazard level is greater than the pre-alarm threshold and less than the emergency threshold, the signal to cause the second hazard detector to generate a second audible pre-alarm speech and activate a second light source in the second color.

4. The hazard detector of claim 1, wherein the user interface module includes a motion detector, and wherein the user input is a specific motion of the user that is detected by the motion detector.

5. The hazard detector of claim 1, further comprising:

a humidity sensor coupled to the processing module, wherein the processing module is further configured to:

receive a reading from the humidity sensor indicating an increase in humidity level, and increase the pre-alarm threshold in response to receiving the reading.

6. The hazard detector of claim 1, further comprising:

a heat sensor coupled to the processing module, wherein the processing module is further configured to:

receive a reading from the heat sensor indicating a rate of increase in temperature that is greater than a heat threshold, and decrease the pre-alarm threshold in response to receiving the reading.

7. The hazard detector of claim 1, wherein the processing module includes a high power processor and a low power processor, wherein the high power processor is operatively coupled to the speaker, and wherein the low power processor is operatively coupled to the horn.

8. A method for providing a pre-alarm of a developing hazardous condition, the method comprising:

detecting a first hazard level, the first hazard level indicating an amount of at least one of smoke and carbon monoxide (CO) present at a hazard detector;

comparing the first hazard level with an emergency threshold;

determining that the first hazard level is greater than the emergency threshold;

activating a horn that generates an audible alarm in response to determining that the first hazard level is greater than the emergency threshold;

activating a first light source that generates a red colored light in response to determining that the first hazard level is greater than the emergency threshold;

detecting a second hazard level;

comparing the second hazard level with the emergency threshold;

determining that the second hazard level is less than the emergency threshold;

comparing the second hazard level with a pre-alarm threshold, the pre-alarm threshold being less than the emergency threshold;

determining that the second hazard level is greater than the pre-alarm threshold;

activating a second light source that generates a yellow colored light in response to determining that the second hazard level is greater than the pre-alarm threshold and less than the emergency threshold;

activating a speaker that generates an audible pre-alarm speech at a lower volume than the horn in response to determining that the second hazard level is greater than the pre-alarm threshold and less than the emergency threshold, the audible pre-alarm speech including content that warns of the developing hazardous conditions;

receiving user input via a user interface module of the hazard detector; and stopping generation of the audible pre-alarm speech in response to receiving the user input.

9. The method of claim 8, further comprising:

not activating the horn in response to determining that the second hazard level is greater than the pre-alarm threshold and less than the emergency threshold.

10. The method of claim 8, further comprising:

detecting a battery level of the hazard detector that is less than a battery threshold;

generating audible battery speech via the speaker in response to detecting the battery level, the audible battery speech including content that warns of a low battery level; and activating the second light source in response to detecting the battery level.

11. The method of claim 8, wherein the audible pre-alarm speech further includes content that warns of the horn being activated to generate the audible alarm.

12. The method of claim 8, wherein the audible pre-alarm speech further includes content indicating a detected hazardous substance.

13. The method of claim 8, wherein the audible pre-alarm speech further includes content indicating a location of the hazard detector.

14. The method of claim 13, wherein the location is a room within an enclosure.

15. A non-transitory computer-readable medium, having instructions stored therein, which when executed cause a computer to perform a set of operations comprising:

detecting a hazard level that indicates an amount of at least one of smoke and carbon monoxide (CO) present at a hazard detector;

comparing the hazard level with an emergency threshold;

determining that the hazard level is less than the emergency threshold;

comparing the hazard level with a pre-alarm threshold, the pre-alarm threshold being less than the emergency threshold;

determining that the hazard level is greater than the pre-alarm threshold;

activating a light source that generates light in a first color, a second color, and a third color, the second color being between the first color and the third color on a color spectrum, the light source being activated in the second color in response to determining that the hazard level is greater than the pre-alarm threshold and less than the emergency threshold;

activating a speaker that generates an audible pre-alarm speech in response to determining that the hazard level is greater than the pre-alarm threshold and less than the emergency threshold, the audible pre-alarm speech including content that warns of a developing hazardous condition;

receiving user input via a user interface module of the hazard detector; and ceasing generation of the audible pre-alarm speech in response to receiving the user input.

16. The non-transitory computer-readable medium of claim 15, wherein the first color is a green color, the second color is a yellow color, and the third color is a red color.

17. The non-transitory computer-readable medium of claim 15, having further instructions stored therein, which when executed cause the computer to perform a set of operations comprising:

modulating the light source to generate a pulse effect that pulses in synchronization with the audible pre-alarm speech.

18. The non-transitory computer-readable medium of claim 15, having further instructions stored therein, which when executed cause the computer to perform a set of operations comprising:

generating a spatiotemporal pattern with the light source.

19. The non-transitory computer-readable medium of claim 15, having further instructions stored therein, which when executed cause the computer to perform a set of operations comprising:

generating a bell or chime sound via the speaker in response to determining that the hazard level is greater than the pre-alarm threshold and less than the emergency threshold.

* * * * *